(12) United States Patent
Lin

(10) Patent No.: US 11,480,574 B2
(45) Date of Patent: Oct. 25, 2022

(54) REAGENT KITS FOR DIAGNOSIS OF HEPATOCARCINOMA

(75) Inventor: Biaoyang Lin, Hangzhou (CN)

(73) Assignee: Biaoyang Lin, Hangzhou (CN)

( * ) Notice: Subject to any disclaimer, the term of this patent is extended or adjusted under 35 U.S.C. 154(b) by 0 days.

(21) Appl. No.: 12/949,420

(22) Filed: Nov. 18, 2010

(65) Prior Publication Data

US 2011/0065098 A1    Mar. 17, 2011

Related U.S. Application Data

(63) Continuation-in-part of application No. 12/992,363, filed as application No. PCT/CN2008/001767 on Oct. 20, 2008, now Pat. No. 11,193,934.

(30) Foreign Application Priority Data

May 21, 2008  (CN) .......................... 200810108528.5

(51) Int. Cl.
    *G01N 33/574*    (2006.01)
    *G01N 33/541*    (2006.01)

(52) U.S. Cl.
    CPC ..... *G01N 33/57438* (2013.01); *G01N 33/541* (2013.01); *G01N 2333/96433* (2013.01); *G01N 2800/7028* (2013.01)

(58) Field of Classification Search
    None
    See application file for complete search history.

(56) References Cited

U.S. PATENT DOCUMENTS

| | | | |
|---|---|---|---|
| 7,083,786 B2 * | 8/2006 | Jensenius et al. | 424/145.1 |
| 7,230,086 B2 * | 6/2007 | Price et al. | 530/388.1 |
| 7,668,661 B2 * | 2/2010 | Volker et al. | 702/19 |
| 2003/0032008 A1 * | 2/2003 | Lim et al. | 435/5 |
| 2003/0082652 A1 | 5/2003 | Holten-Andersen | |
| 2006/0019256 A1 * | 1/2006 | Clarke | C12Q 1/6886 435/6.14 |

OTHER PUBLICATIONS

Schmidt, Henrik, et al. "Elevated serum level of YKL-40 is an independent prognostic factor for poor survival in patients with metastatic melanoma." Cancer: Interdisciplinary International Journal of the American Cancer Society 106.5 (2006): 1130-1139.*
Wikipedia, "MASP2 (protein)," (https://en.wikipedia.org/wiki/MASP2_(protein)), 3 pages, as downloaded Mar. 9, 2022.*
Wikipedia, "CHI3L1," (https://en.wikipedia.org/wiki/CHI3L1), 5 pages, as downloaded Mar. 9, 2022.*
Johansen, Julia S., et al. "Is YKL-40 a new therapeutic target in cancer?." Expert opinion on therapeutic targets 11.2 (2007): 219-234.*
Hycult, "Complement and Apoptosis," Hycult Scope, Hycult Biotech, downloaded from (https://www.hycultbiotech.com/media/wysiwyg/HCS-Apoptosis_2006-3-HR.pdf) on Jan. 18, 2022, 4 pages.*
Schlapbach, Luregn J., et al. "Deficiency of mannose-binding lectin-associated serine protease-2 associated with increased risk of fever and neutropenia in pediatric cancer patients." The Pediatric infectious disease journal 26.11 (2007): 989-994.*
Lomholt, Anne F., et al. "The serological markers TIMP-1, PAI-1, MASP-2 and CRP are independent predictors of colorectal cancer-specific death." (2006): 1346-1346.*

* cited by examiner

*Primary Examiner* — G Steven Vanni
(74) *Attorney, Agent, or Firm* — Weisun Rao; Sunyong Tang; Venture Partner, LLC

(57) ABSTRACT

The present invention relates to reagent kits for *in vitro* measurement of YKL-40 and MASP2 and diagnosis of hepatocarcinoma of a test individual.

4 Claims, 3 Drawing Sheets

REAGENT KITS FOR DIAGNOSIS OF HEPATOCARCINOMA

CROSS REFERENCE

This is a continuation-in-part of and claims priority to U.S. application Ser. No. 12/992,363, filed on Nov. 12, 2010, which is a national phase application of and claims the benefits to PCT/CN2008/001767 under 35 U.S.C. § 371, which in turns claims the benefit of Chinese Patent Application No. 200810108528.5, filed on May 21, 2008, all of which are incorporated herein by reference in their entireties.

TECHNICAL FIELD OF THE INVENTION

The present invention pertains to the technical field of biomedicine. Specifically, the present invention relates to a method to improve the accuracy of sample classification and a reagent kit used to detect YKL-40 and MASP2 proteins in the samples.

BACKGROUND OF THE INVENTION

Hepatocarcinoma (HCC) is a frequently-encountered and lethal malignant tumor. According to statistics, the number of HCC patients increases by about 500,000 annually and about 500,000 patients die of this disease annually (see, e.g., D. M. Parkin, F. Bray, J. Ferlay, and P. Pisani, (2001) Estimating the World Cancer Burden, Globocan 2000 *Int. J. Cancer,* 94, 153-156). The current approaches for the diagnosis of HCC include ultrasonic detection and alpha-fetoprotein (AFP) detection, which are usually used together (see, e.g., Spangenberg, H. C., Thimme, R., and Blum, H. E., Serum markers of hepatocellular carcinoma, *Semin. Liver Dis.,* 2006, 26, 385-390). When AFP is used as the biomarker for HCC diagnosis through the receiver operator characteristic (ROC) curve which reflects the selectivity and specificity of the diagnosis, the positive threshold of detection is usually 20 ng/mL (see, e.g., J. Chen and P. Fan, Preparation of an immunochromatographic strip for quick AFP detection, *Journal of Analytical Science,* 2002 (4), 273-276). The sensitivity and specificity of ultrasonic-AFP joint detection are respectively 50~85% and 70~90%. But its false positive and false negative rate is as high as 40% (see, e.g., D. G. Tu, S. T. Wang, T. T. Chang, N. T. Chiu, and W. J. Yao, The value of serum tissue polypeptide specific antigen in the diagnosis of hepatocellular carcinoma, *Cancer,* 1999, 85, 1039-1043; Buscarini, L., Sbolli, G., Cavanna, L., Civardi, G., Di Stasi, M., Buscarini, E., and Fomari, F., Clinical and diagnostic features of 67 cases of hepatocellular carcinoma, *Oncology,* 1987, 44, 93-97). Therefore, there is an urgent need for developing an HCC diagnosis approach which provides easier detection, higher sensitivity and specificity, and higher accuracy.

YKL-40 is an abbreviation of human cartilage glycoprotein 39 (HcGP.39) or chitinase 3-like 1 (which is abbreviated as CH13L1). Research has revealed that the level of YKL-40 in serum is related to many disease conditions such as osteoarthritis, primary colorectal carcinoma, breast carcinoma, and recurrent oophoroma and can be used for the diagnosis, prognosis evaluation, and monitoring of treatment effect and disease progression of some diseases. For example, it can be used for the diagnosis and prognosis of oophoroma (see, e.g., M. Cheng et al., Application of serum YKL-40 in the diagnosis and prognosis of oophoroma patients, *Guangdong Medical Journal,* 2008, 29(2): 255-256). In an essay published in the *New England Journal of Medicine* on Nov. 15, 2007, researchers of Yale School of Medicine stated that results of clinical experiments indicated that this molecule may play an important role in the determination of the physiological reactions to severe asthma. Compared with normal people, asthma patients have more YKL-40-circulating serum, which is also related to the severity of asthma. Johansen et al. of the University of California at San Diego stated that YKL-40 is a biomarker independent of carcinoembryonic antigen (CEA) and lactin dehydrogenase (LDH), normal people having high levels of YKL-40 are exposed to 2.7 times as much risk of gastrointestinal tumor as others and usually have poor prognosis after being diagnosed as having gastrointestinal tumor. It has also been discovered that the level of serum YKL-40 can be used as an indicator of hepatic fibrosis (see,e.g., J.S. Johansen, P. Christoffersen, S. Moiler, P.A. Price, J.H. Henriksen, C. Garbarsch, and F. Bendtsen, Serum YKL-40 is increased in patients with hepatic fibrosis, *Journal of Hepatology,* 2000, 32, 911-920). However, there have not been reports about the application of YKL-40 detection in HCC diagnosis.

MASP2 is the abbreviation of mannan-binding lectin associated serine protease-2. It is related to human immunodeficiency diseases and plays an important role in the innate immune defense of the organism (see, e.g., Xuemin Cai et al., Prokaryotic expression of mannan-binding lectin associated serine protease-2 in N-end segments, *Journal of Immunology,* 2007, 3, 235-238). But there have not been reports its application in HCC diagnosis.

Research by the inventor has revealed that MASP2 gene is specifically expressed in the liver. The inventor unexpectedly found that both proteins (YKL-40 and MASP2) are related to HCC. Specifically, the blood serum of HCC patients has significantly higher level or concentration of YKL-40 than normal samples while the expression of MASP2 is lower in HCC patients than in normal samples. Therefore the inventor proposed that by combining a protein having high expression in carcinoma (this protein may not be specific to a certain carcinoma and may be highly expressed in different types of carcinoma) with a protein having low expression in a specific tissue or organ (down-regulation of the specific protein executing specific functions of the tissue or organ due to the carcinoma), one can obtain a joint biomarker for cancer diagnosis. This joint marker will improve the sensitivity and specificity of cancer detection. The inventor has taken the YKL-40 and MASP2 proteins as examples to check if they can be used as a biomarker for the clinical application to HCC and if their joint detection can improve the accuracy of diagnosis and prognosis of the disease and the results have validated the inventor's proposal.

BRIEF DESCRIPTION OF THE INVENTION

The present invention is based on the unexpected findings described above.

In some aspect, the present invention provides methods for improving the accuracy of sample classification through joint-detection of the YKL-40 and MASP2 proteins in the samples. The joint detection comprises: (1) detection of the YKL-40 and MASP2 contents in sample; (2) algorithmic analysis of the measured YKL-40 and MASP2 contents, and (3) classification of the test sample according to the algorithmic analysis results. These methods can be used in the diagnosis, prognosis evaluation, and monitoring of treatment effect and disease course of various cancers such as hepatocarcinoma.

In some embodiments of these methods, the concentrations of YKL-40 and MASP2 are measured separately. In some other embodiments, the algorithmic analysis is to draw ROC curves that reflects sensitivity and specificity of the measurements, wherein the concentrations if YKL-40, the concentrations of MASP2, and the ratios of the YKL-40 and MASP2 concentrations are used as variables to draw ROC curves, and the area under curve (AUC) is calculated; then the samples are classified according to the desired sensitivity and specificity according to different threshold values. In still some other embodiments, the concentration of at least one of YKL-40 and MASP2 is measured by ELISA, the Lowery assay, the Bradford assay, the BCA assay, UV absorbance, or any modification based thereon.

The samples that are suitable for the methods of this invention can be selected from the group consisting of whole blood, blood plasma, blood serum, urine, cerebrospinal fluid, saliva, and tear.

In another aspect, the invention provides reagent kits for the detection of YKL-40 and MASP2 proteins in a sample. Each of such reagent kits comprises: (1) antibodies capable of binding YKL-40 and MASP2, and (2) antibodies capable of binding YKL-40 and MASP2 when YKL-40 and/or MASP2 are bound by antibodies stated in (1). In some embodiments, the reagent kits may further include: (3) standard samples composed of solutions containing known concentrations of YKL-40 and MASP2, and (4) antibody markers for detection, which can bind antibodies to form conjugates. In some embodiments, the antibodies in (1) or (2) are capable of binding virus such as hepatitis virus.

In yet another aspect, the invention provide reagent kits each including (1) antibodies capable of binding hepatitis virus, YKL-40, and MASP2, and (2) antibodies capable of binding hepatitis virus and/or YKL-40 and MASP2, when hepatitis virus and/or YKL-40 and/or MASP2 are bound by the binding antibodies stated in (1).

Still another aspect of this invention further provides methods for improving the sensitivity of sample analysis through joint-detection of a carcinoma (or cancer) high expression protein and a tissue or organ specific expression protein in the sample. Each method comprises the steps of: (1) measurement of the content of carcinoma high expression protein in the sample of the individual; (2) measurement of the content of specifically expressed protein in a certain tissue or organ in the sample of the individual; (3) algorithmic analysis of the measured carcinoma high expression protein and tissue or organic specific expression protein, and (4) classification of the individual as having cancer or being healthy according to the algorithmic analysis results. In some embodiments, the protein of high-level expression is YKL-40. In some other embodiments, the protein of low-level expression is MASP2. In still some other embodiments, the protein of high-level expression is YKL-40 and the protein of low-level expression is MASP2.

Yet still a further aspect of the present invention provides a reagent kit used for the detection of a carcinoma high expression protein and a tissue or organ specific expression protein in the sample. Each reagent kit comprises: (1) antibodies capable of binding carcinoma high expression protein and tissue or organ specific expression protein, and (2) marking antibodies capable of binding the carcinoma high expression protein and tissue or organ specific expression protein when the carcinoma high expression protein and/or tissue or organ specific expression protein are bound by the antibodies stated in (1).

By using the method and reagent kit of the present invention for the joint detection of the proteins YKL-40 protein and MASP2 in the samples of the individual, one can effectively increase the sensitivity, specificity, and accuracy of diagnosis, prognosis evaluation, evaluation of treatment effect, and monitoring of disease course of many diseases such as cancer (e.g., hepatocarcinoma).

Accordingly, the invention further provides methods for detecting the occurrence of a cancer in an individual, each including: taking a test sample of the individual to be detected and a control sample of another individual free of the cancer, and measuring the concentrations of a first set of disease specific and a second set of tissue or organ specific proteins in the test sample and comparing their concentrations to those in the control sample, wherein the higher concentrations of the first set of disease specific protein and the lower concentrations of the second set of tissue or organ specific proteins in the test sample than the concentrations of the same proteins in the control sample are an indication of the occurrence of the cancer.

In some embodiments, the cancer is hepatocarcinoma.

In some other embodiments, the first set of disease specific proteins are cancer over expression proteins. This first set of proteins may include YKL-40.

In some other embodiments, the second set of proteins includes a set of tissue or organ specific or enriched expression proteins. This second set of proteins may include MASP2. Examples of such tissue or organ include, but are not limited to, liver, breast, ovary, lung, prostate, bladder, mouth, nose, kidney, stomach, throat, pancreas, heart, ovary, colon, brain, skin, and bone.

In some specific embodiments, the first set of proteins contains YKL-40 and the second set of proteins contains MASP2.

In still some other embodiments, the test sample and control sample are whole blood, blood plasma, blood serum, urine, cerebrospinal fluid, saliva, or tear.

Also within the scope of this invention are methods for determining the efficacy of a drug in treating a cancer in an individual, which include measuring the concentrations of a first set of disease specific proteins and a second set of tissue or organ specific proteins in the samples of the subject at different times of the treatment, wherein: (a) the presence of the cancer is indicated by the higher expression of the first set of disease specific proteins and lower expression of the second set of tissue or organ specific proteins than those in an individual free of the cancer, and (b) the decrease of the concentrations of the first set of disease specific proteins and the increase of concentrations of the second set of tissue or organ specific proteins in the samples of the cancerous subject during the treatment indicates that the severity of the cancer has decreased.

In some embodiments, the cancer is hepatocarcinoma. In some other embodiments, the samples are whole blood, blood plasma, blood serum, urine, cerebrospinal fluid, saliva, or tear.

In still some other embodiments, the first set of proteins contains YKL-40. In other embodiments, the second set of proteins contains MASP2.

DETAILED DESCRIPTION OF THE INVENTION

Figure 1:
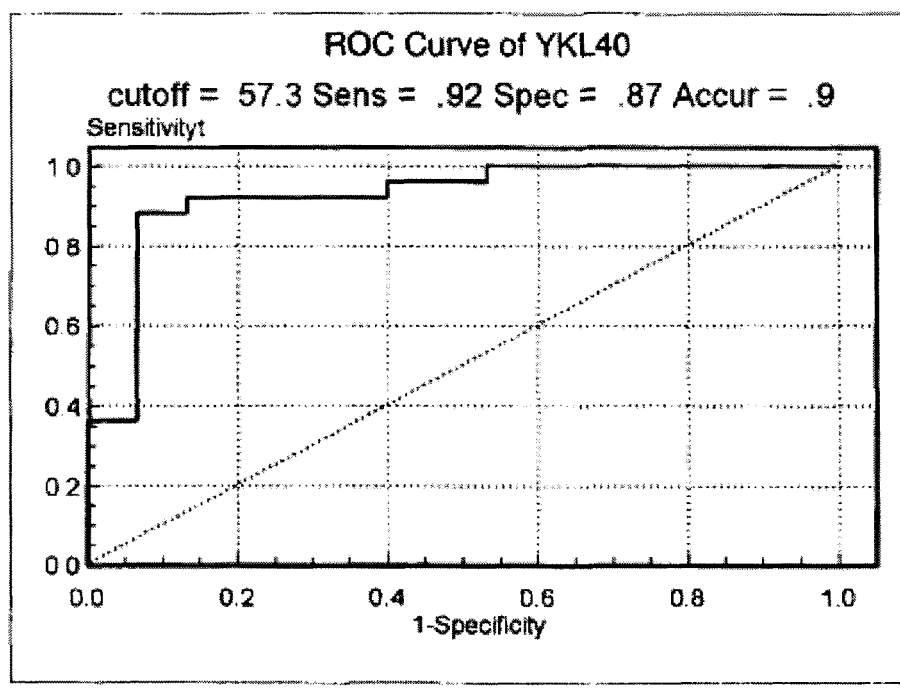
FIG. 1 is the ROC curve of the detection of YKL-40 in the serum samples of HCC patients.

The present invention will be further described with detailed embodiments and attached drawings. It is to be expressly understood that the following embodiments are set forth as examples and not by way of limitations on the invention as ultimately defined in the claims.

It is known to all that when an individual is afflicted by cancer or is in the clinical stage of cancer, cancer associated virus or cancer associated genes will be highly expressed. Such highly expressed proteins, such as YKL-40, can be used as biological markers of cancer. On the other hand, functions of related tissues or organs of the individual will decline, resulting in reduced levels of proteins which are specifically expressed in such tissues or organs, such as MASP2 which is specifically expressed in the liver. Therefore the low expression levels of proteins specifically expressed in tissues or organs also have the potential to serve as biological markers of cancer. It is well known by those having ordinary skill in the art that tests with a single biological marker often results in high false positive or false negative rates and thus reduce the accuracy or utility of a clinical test. Therefore, both the contents of carcinoma high expression proteins in the sample of the individual, such as YKL-40, and the low expression levels of proteins specifically expressed in certain tissues or organs, such as MASP2 which is specifically expressed in the liver, are measured at the same time. In other words, new markers are added on the basis of original pairing markers in order to improve the sensitivity of the detection. This method will increase the sensitivity of cancer tests and will be verified in the following embodiments.

It is beyond doubt that the methods and corresponding reagent kits provided by the present invention for improving the sensitivity of cancer detection of individuals can be used in the diagnosis, prognosis evaluation, evaluation of treatment effect, and monitoring of disease course of all kinds of cancer and pathogenic changes in the organs.

Take joint detection of blood samples for example. The application of the present invention to the cancer or disease of a specific tissue or organ comprises the following steps: assay of high-level expression proteins or genes of cancer or disease in the blood sample of the individual; assay of low-level expression of tissue-specific or organ-specific proteins or genes in blood; algorithmic analysis of the measured protein content or gene expression results; and classification of the measured sample of the individual according to the algorithmic analysis results in order to obtain diagnosis result of the cancer or disease. The result may be: healthy, early-stage cancer or disease, mid-term cancer or disease, or terminal cancer or disease.

It should be understood that the term "joint detection" used herein not only comprises the measurement of the contents of specific combinations of proteins in the sample, but also comprises the algorithmic analysis of the measured protein contents. It further comprises the classification of the test sample according to the results of algorithmic analysis.

ELISA

The ELISA technology is used in the present invention for the detection of carcinoma high expression proteins, such as YKL-40, and tissue or organ specific expression proteins, such as MASP2, in the sample of the individual.

ELISA (enzyme linked immunosorbent assay) is a commonly-used protein content analysis method in molecular biology. It can be used to measure both antigens and antibodies. Many other types of assay can be adopted in the present invention according to the source of reagent, characters of the sample, and the detection conditions, such as: Double antibody sandwich method, two-site one-step method, and indirect method for the assay of antibodies, competition method and capture method for the assay of IgM antibody, and ELISA with the use of avidin and biotin.

Other Assays

Other methods that can be used to measure the level or concentration of the proteins include the Lowery assay, the Bradford assay, the BCA assay, UV absorbance, or any modification based thereon. For a description about these methods, see, e.g., Bradley J. S. C. Olson and John Markwell (Contr.), *Current Protocols in Biological Science*, 3.4.1-3.4.29, John Wiley & Sons, Inc. (2007), which is incorporated herein by reference in its entirety.

Reagent Kit

A reagent kit is preferred for the ELISA of the present invention as it can realize quick operation and avoid the complicated and troublesome routine experimental detection. The ELISA kit of the present invention comprises a YKL-40 immunoenzymatic standard kit, a MASP2 immunoenzymatic standard kit, and YKL-40 and MASP2 detection kits. YKL-40 and MASP2 detection kits are preferred in order to improve the sensitivity, specificity, and accuracy of disease diagnosis. They can be used respectively or simultaneous to measure two groups of detection results in order to provide quick effects.

The YKL-40 and MASP2 detection kits of the present invent shall at least comprise (1) antibodies capable of binding YKL-40 and MASP2, and (2) antibodies capable of binding YKL-40 and MASP2 when YKL-40 and/or MASP2 are bound by the antibodies stated in (1). The antibodies of (1) and (2) can also be referred to as binding antibodies and marked antibodies or marking antibodies.

The reagent kits mentioned above may further comprise (3) standard samples composed of solutions containing known amounts of YKL-40 and MASP2, which may come from the bacterial expression of gene engineering, animals, or human body fluid, and (4) antibody markers, such as enzyme labels like horse radish peroxidase or fluorescent marks in the reported methods, which can bind antibodies to form conjugates for detection.

A more preferred kit may further comprise at least one of the following components: (5) a carrying tool, whose space is divided into compartments to hold one or several vessels, 96-well plates, or strips, wherein the vessels may be vials, test tubes, and similar articles and each vessel contains an independent component used in the method of the present invention; (6) auxiliary reagents, such as color development reagent, enzyme inhibitor, buffer solutions, stabilizing agent, diluting agent, rinsing reagent, and similar reagents; (7) instructions of use which may be written on vials, test tubes, and similar articles, or on a separate piece of paper, or outside or inside the vessels, or in the form of multimedia such as CD, computer compact disc, or video.

Preferred antibodies can be fixed on solid-state carriers to form capture antibodies.

The antibodies may be any antibody segments capable of binding YKL-40 and MASP2 and may be recombinants, chimeric antibodies, humanized antibodies, and murine antibodies or antibodies from other animal species (e.g., rabbit, sheep, horse, or camel). Such antibodies may be monoclonal antibodies or polyclonal antibodies, although monoclonal antibodies are preferred.

The preferred antibody conjugate can be put to photometry with ELISA readers such as ELIASA.

Samples

Samples used by the present invention can include multiple forms, such as whole blood, blood plasma, blood serum, urine, cerebrospinal fluid, saliva, or tear. Blood serum is preferred.

Samples can be prepared by normal methods such as centrifugation, e.g., as described in the following references: Young, D. S. & Bermes, E. W., "Specimen collection and processing" in Tietz Textbook of Clinical Chemistry, 2nd Edition, Eds. Burtis, C. A. & Ashwood, E. R., Saunders (1994); Methods in Enzymology, H. Van Vunakis and J. J. Langone (Eds), 1981, 72(B); Practice and Theory of Enzyme Immunoassays, P. Tijssen, Laboratory Techniques in Biochemistry and Molecular Biology, R. J. Burden and P. H. Van Knippenberg (Eds.), Elsevier, 1985; Introduction to Radioimmunoassay and Related Techniques, T. Chard, ibid, 3rd Edition, 1987; Methods in Enzymology, H. Van Vunakis and J. J. Langone (Eds), 1981, 74(C).

ROC Curve

After measuring, e.g., by ELISA, the concentrations of carcinoma high expression proteins, such as YKL-40, and tissue or organ specific expression proteins, such as MASP2, in the samples, we use algorithmic analysis or other statistic analysis for the measured concentrations of carcinoma high expression proteins, such as YKL-40, and tissue or organ specific expression proteins, such as MASP2 in the samples, to derive a classification standard having significance for sample classification. This algorithmic method is preferably done with a computer. For example, the data can be used to draw an ROC curve and then to classify the samples of individuals.

The full name of ROC curve is receiver operator characteristic curve, also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC) is, the higher is the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high.

The ROC curve evaluation method is different from the traditional evaluation methods in that intermediate states are allowed in accordance with the actual situation. The test results can be divided into several ordered classes such as normal, basically normal, suspicious, basically abnormal, and abnormal.

When it comes to the diagnosis of diseases, the ordered classes mentioned above can be divided into negative, uncertain, and positive. When it comes to the diagnosis of diseases, the ordered classes mentioned above can be further divided into cancer and healthy.

Therefore according to the example of the detection of YKL-40 and MASP2 proteins in the samples, the method of the present invention to improve the accuracy of sample classification may comprise the following steps: (1) respectively determine the YKL-40 and MASP2 concentrations in the samples; (2) draw an ROC curve with the ratio between YKL-40 content and MASP2 content as the variable according to the sensitivity and specificity values of different thresholds to the diagnosis of cancer, and then calculate the area under the curve (AUC), and (3) classify the test sample according to the expected sensitivity and specificity (cancer or healthy).

Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE—ROC.SAS, GB STAT V10.0 (Dynamic Microsystems, Inc. Silver Spring, Md., USA), etc.

Diagnosis, Prognosis Evaluation, and Monitoring of Treatment Effect or Disease Course of HCC The present invention—including both the methods and reagent kits described above—can be used in the diagnosis, prognosis evaluation, and monitoring of treatment effect of various diseases and their states, such as cancer (e.g., HCC). It is known to all that the disease course of hepatitis is closely related to the conversion to HCC. The typical disease course could be: Hepatitis (e.g. hepatitis B or hepatitis C)->cirrhosis->HCC or Hepatitis->HCC. Research by the inventor has already revealed that the expression of hepatitis virus can also be used as a biological marker for HCC detection and that combining the expressions of YKL-40 and MASP2 for joint detection can significantly improve the success ratio of HCC diagnosis. For this sake, the present invention further provides a method for the diagnosis, prognosis evaluation, and monitoring of treatment effect or disease course of hepatocarcinoma, comprising: detection of the expression of hepatitis virus in the blood sample of the individual; detection of the expression of YKL-40 and MASP2 in the blood sample of the individual; algorithmic analysis of the measured expression levels of hepatitis virus and YKL-40 and MASP2; and classification of the measured blood sample according to the algorithmic analysis results in order to obtain the judgment result of HCC. The result may be: early-stage HCC, mid-term HCC, or terminal HCC.

The expression of hepatitis virus can be done with the standard methods in the art, such as standard blood sample test paper method, blood sample reagent kit method, and routine blood sample test method, etc.

It is obvious that integrating the expression of hepatitis virus, YKL-40 and MASP2 of blood sample into the same reagent kit will make HCC detection more convenient, time-efficient, and economical. For this sake, the present invention further provides a joint-test kit for the diagnosis, prognosis evaluation, and monitoring of treatment effect or disease course of HCC, which at least comprises: (1) binding antibodies—antibodies capable of binding hepatitis virus, YKL-40 and MASP2, and (2) marked or marking antibodies—antibodies capable of binding hepatitis virus and/or YKL-40 and MASP2 YKL-40 when hepatitis virus and/or YKL-40 and/or MASP2 are bound by antibodies stated in (1). The preferred reagent kit may further comprise: (3) standard samples composed of solutions containing known amounts of hepatitis virus, YKL-40 and MASP2, which may come from the bacterial expression of gene engineering, animals, or human body fluid, and (4) antibody markers, such as enzyme labels like horse radish peroxidase or fluorescent marks in the reported methods, which can bind antibodies to form conjugates for detection.

The present invention will be further described in detain with the example of the HCC diagnosis of individual blood serum as the sample.

Example 1

Sample Collection 1 mL blood serum was taken from each of the 25 cases of HCC patients aged between 50 and 60 as the positive control. 1 mL normal blood serum was taken from each of the 15 cases of healthy volunteers aged between 50 and 60 for YKL-40 and MASP2 concentration test.

Measurement of YKL-40 Concentration

A YKL-40 kit produced by Quidel Company (San Diego, Calif., USA) and a Bio-Rad 680 ELIASA (US) were used for ELISA operation in accordance with the manufacturers' instructions. The operation included the steps of:
1. Allowing pouch of Coated Strips to equilibrate to 18-28° C. before opening; removing Stripwell Frame and the required number of Coated Strips from the pouch; ensuring that the pouch containing unused strips was completely resealed and contains desiccant; the total number of specimens to be tested and the number of specimens for quality control were calculated; and each specimen needed one antigen-coated well and three replicates were performed for each sample.
2. Placing desired number of Coated Strips in Stripwell Frame.
3. Adding 20 µL Standard, Control, or sample to each well of the Coated Strips, which was completed within 30 minutes.
4. Adding 100 µL of Capture Solution to each well; dispensing Capture Solution with sufficient force to ensure adequate mixing; and tapping Stripwell Frame several times.
5. Incubating for 60±5 minutes at 18-28° C.
6. Manually inverting/emptying strips. Adding at least 250 µL of 1× wash buffer to each well and manually inverting/emptying strips. Repeating three more times for a total of four washes. Vigorously blotting the strips dry on paper towels after the last wash.
7. Adding 100 µL of reconstituted Enzyme Conjugate to each well; discarding remaining reconstituted Enzyme Conjugate after use.
8. Incubating for 60±5 minutes at 18-28° C.
9. Repeating wash as indicated in step 6.
10. Adding 100 µL of Working Substrate Solution to each well.
11. Incubating for 60±5 minutes at 18-28° C.
12. Adding 100 µL of Stop Solution to each well. Adding Stop Solution in the same pattern and time intervals as the Working Substrate Solution addition.
13. Reading the optical density at 405 nm. Assuring that no large bubbles are present in wells and that the bottom of the strips are clean. Strips should be read within 15 minutes of Stop Solution addition.
14. using a linear calibration curve "Y=mx+b" to analyze the result of YKL-40 or MASP-2;
15. using the standard curve to read the concentrations of YKL-40 or MASP2 in the blood serum sample or control solution.

Results:
Table 1 below shows the detection results obtained through the steps described above.

TABLE 1

| Sample No. | Diagnosis result | Protein concentration in serum (ng/mL) | | YKL-40/MASP-2 ratio |
|---|---|---|---|---|
| | | YKL-40 | MASP-2 | |
| 1 | HCC | 782.2 | 1359.9 | 57.52 |
| 2 | HCC | 76.8 | 250.2 | 30.7 |
| 3 | HCC | 705 | 195.7 | 360.25 |
| 4 | HCC | 1444.6 | 90.3 | 1599.78 |
| 5 | HCC | 165.3 | 281.75 | 58.67 |
| 6 | HCC | 98.7 | 248.4 | 39.73 |
| 7 | HCC | 317.2 | 58.5 | 542.22 |
| 8 | HCC | 354.1 | 81.6 | 433.95 |
| 9 | HCC | 211.7 | 167.2 | 126.61 |
| 10 | HCC | 87.8 | 33.9 | 259 |
| 11 | HCC | 734.4 | 292.9 | 250.73 |
| 12 | HCC | 184.4 | 935.9 | 19.7 |
| 13 | HCC | 94.6 | 206.4 | 45.83 |
| 14 | HCC | 313 | 208.3 | 150.26 |
| 15 | HCC | 137.3 | 124.7 | 110.1 |
| 16 | HCC | 475.3 | 241.6 | 196.73 |
| 17 | HCC | 66.5 | 282.7 | 23.52 |
| 18 | HCC | 177.62 | 244.54 | 72.63 |
| 19 | HCC | 59.96 | 426.67 | 14.05 |
| 20 | HCC | 44.96 | 80.29 | 56 |
| 21 | HCC | 99.9 | 630.05 | 15.86 |
| 22 | HCC | 115.68 | 215.56 | 53.66 |
| 23 | HCC | 183.47 | 339.71 | 54.01 |
| 24 | HCC | 440.81 | 106.86 | 412.51 |
| 25 | HCC | 36.09 | 244.06 | 14.79 |
| 26 | Healthy | 34.4 | 185 | 18.59 |
| 27 | Healthy | 21.5 | 171 | 12.57 |
| 28 | Healthy | 57.3 | 724 | 7.91 |
| 29 | Healthy | 54 | 443.9 | 12.16 |
| 30 | Healthy | 62.9 | 356.2 | 17.66 |
| 31 | Healthy | 47.5 | 330.7 | 14.36 |
| 32 | Healthy | 25.8 | 699.9 | 3.69 |
| 33 | Healthy | 43.8 | 837.7 | 5.23 |
| 34 | Healthy | 48.5 | 470.5 | 10.31 |
| 35 | Healthy | 16.7 | 384.2 | 4.35 |
| 36 | Healthy | 14.8 | 739.4 | 2 |
| 37 | Healthy | 39.6 | 469.4 | 8.44 |
| 38 | Healthy | 11 | 363.2 | 3.03 |
| 39 | Healthy | 10.4 | 330.1 | 3.15 |
| 40 | Healthy | 265.8 | 530.1 | 50.14 |

The data in Table 1 indicate that the concentration of YKL-40 was closely correlated to HCC. In other words, the level of YKL-40 protein in the blood serum of HCC patients was significantly higher than the level of YKL-40 protein in the blood serum of healthy volunteers.

Drawing ROC Curve

A GB STAT V10.0 system (Dynamic Microsystems, Inc., Silver Spring, Md., USA) was used to draw the ROC curve with the level of YKL-40 protein as the variable according to the sensitivity and specificity values of different thresholds to the diagnosis of cancer, and then the area under the curve (AUC) was calculated. The ROC curve and calculation of AUC are shown in FIG. 1.

FIG. 1 shows that the AUC of the ROC curve is 0.98. When the threshold value of the concentration of YKL-40 is 0.87 (ng/mL), the sensitivity of HCC diagnosis is 0.92 (i.e. 92%), the specificity is 0.87 (i.e. 87%), and the success ratio of HCC diagnosis is 0.9 (i.e. 90%).

Example 2

Measurement of MASP2 Concentrations

Similar steps to those of Example 1 were used. The differences included: the concentration of MASP2 protein in blood serum sample was measured with a MASP2 kit produced by Dutch Hycult Biotechnology Company (Uden, Holland) in accordance to the ELISA operation instructions provided by the manufacturer.

The test results are included in Table 1 and show that the concentrations of MASP2 were also closely correlated to HCC. In other words, the concentrations of MASP2 protein in the blood serum of HCC patients were significantly higher than the content of MASP2 protein in the blood serum of healthy volunteers.

Drawing ROC Curve

Figure 2:
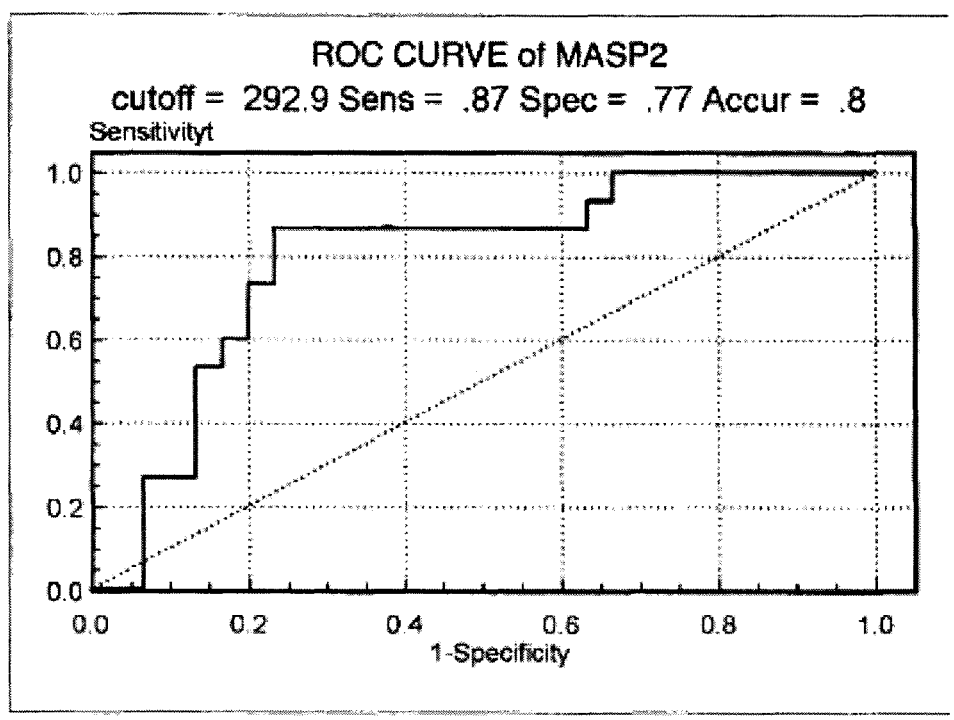
FIG. 2 is the ROC curve of the detection of MASP2 in the serum samples of HCC patients.

A GB STAT V10.0 system is used to draw an ROC curve with the content of MASP2 protein as the variable according to the sensitivity and specificity values of different thresholds to the diagnosis of cancer, and then to calculate the area under the curve (AUC), as shown in FIG. 2.

FIG. 2 shows that when the threshold value of the concentration of MASP2 is 292.9 (ng/mL), the sensitivity of HCC diagnosis is 0.87, the specificity is 0.77 (i.e. 87%), and the actual success ratio of HCC diagnosis is 0.8.

Example 3

YKL-40 and MASP2 were combined. In other words, the GB STAT V10.0 system was used to draw an ROC curve with the ratio between the concentration of YKL-40 protein and the concentration of MASP2 protein as the variable according to the sensitivity and specificity values of different thresholds to the diagnosis of cancer, and then to calculate the area under the curve (AUC), as shown in FIG. 3.

Figure 3:
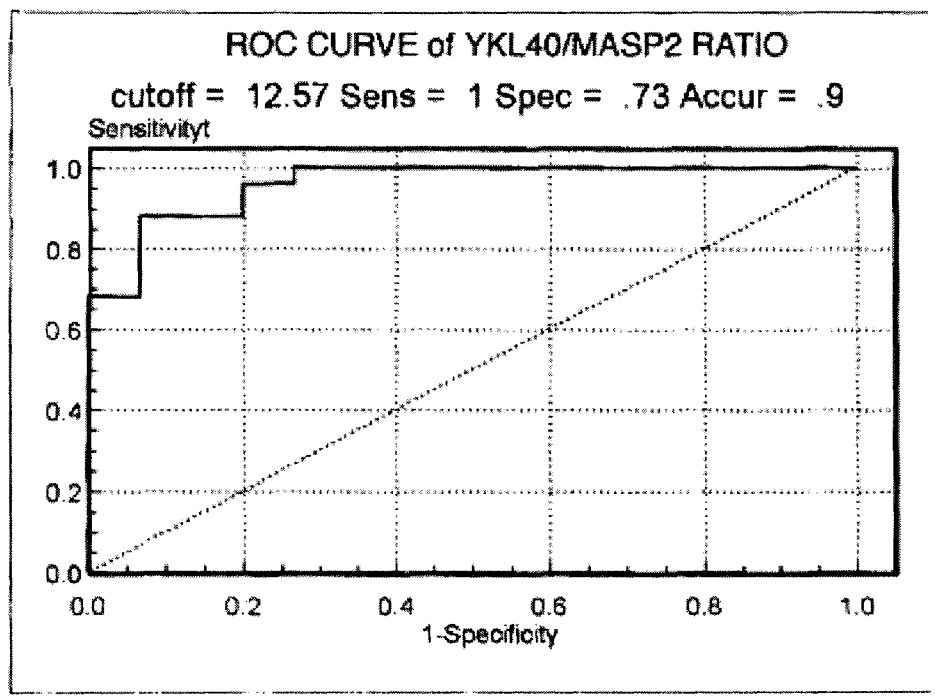
FIG. 3 is the ROC curve of the ratio of YKL-40 to MASP2 in the serum samples of HCC patients.

FIG. 3 shows that when the threshold value is 12.57 (ratio), the sensitivity of HCC diagnosis is 100% and the actual success ratio of HCC diagnosis is 90%. The success ratio is far greater than that (usually 70%) of AFP detection which is being commonly used today.

In addition, by comparing FIG. 3, FIG. 1, and FIG. 2, we can see that when the threshold is 12.57, the sensitivity of HCC diagnosis under joint detection of YKL-40 and MASP2 is higher than that of any single marker (the sensitivity under joint detection is 1, and the sensitivity values of single YKL-40 and MASP2 are respectively 0.92 and 0.87) and the actual success ratio of HCC diagnosis is 0.9.

The technical solution of the present invention has been explained with the example of HCC diagnosis above, wherein an independent YKL-40 or MASP2 kit is used for ELISA operation and the ROC curve of joint detection of YKL-40 and MASP2 is drawn. However, in accordance with the disclosure of the present invention, the method of this invent can absolutely be extended to the diagnosis, prognosis evaluation, and monitoring of treatment effect and development of some other diseases, which is obvious to those having ordinary skill in the art. Therefore, alterations and modifications may be made by those having ordinary skill in the art without departing from the spirit and scope of the invention, and such alterations and modifications are also defined to be within the scope of the invention.

Example 4

The method of this invention for determining the efficacy of a drug in treating a cancer in an individual can be performed by measuring the concentrations of marker proteins in samples of the human tissue of organ that carries the cancer. Specifically, samples (e.g., of whole blood, blood plasma, blood serum, urine, cerebrospinal fluid, saliva, or tear) of the diseased organ or tissue in an individual are first collected, and the concentrations of a first set of disease specific proteins (i.e., marker proteins, e.g., YKL-40) and those of a second set of disease specific proteins (i.e., marker protein, e.g., MASP2) in the samples are measured. Then the drug is administered to the individual with the disease at different times, and samples of the same individual are collected at different times of the drug administration course. The concentrations of the same two sets of the marker proteins are also measured in all the collected samples. The concurrent change in concentration of these two sets of marker proteins indicates the change in the seriousness or state of the disease, thus indicating the efficacy of the drug. If the cancer is hepatocarinoma (HCC), then decrease in the concentration of YKL-40 and increase in the concentration of MASP2, at the same time, would indicate that this drug may be effective in treating HCC.

Many specific marker proteins for various cancers other than HCC have been described in the literature. See, e.g., U.S. Pat. No. 5,773,215; N. Seppa, Science News, 2010; 177: 11, 15 (breast cancer patients typically have higher blood concentration of EGFR, or epidermal growth factor receptor, a cell-surface receptor protein that can trigger pro-growth behavior in a cell, such as proliferation, survival and migration. These known marker proteins may also be used as tools for this method.

The contents of all publications cited are incorporated herein by reference in their entireties.

What is claimed is:

1. A reagent kit for in vitro measurement of YKL-40 and MASP2 and diagnosis of hepatocarcinoma of a test individual, comprising:
   (1) first capture antibodies configured for capturing YKL-40, wherein the first capture antibodies are fixed on a first solid-state carrier;
   (2) second capture antibodies configured for capturing MASP2, wherein the second capture antibodies are fixed on a second solid-state carrier; and
   (3) detection antibodies configured for detecting YKL-40 or MASP2 when YKL-40 or MASP2 is bound by the antibodies stated in (1) or (2).

2. The reagent kit according to claim 1 further comprising:
   (4) standard samples composed of solutions containing known concentrations of YKL-40 and MASP2, and
   (5) enzymes and substrates configured for detection of concentration of YKL-40 or MASP2.

3. The reagent kit according to claim 1 further comprising enzyme labels which are configured to bind antibodies to form conjugates for detection.

4. The reagent kit according to claim 1 further comprising:
   a carrying tool, whose space is divided into compartments configured to hold one or several vessels, 96-well plates, or strips, wherein the vessels comprise vials or test tubes; and/or
   an auxiliary reagent selected from color development reagent, enzyme inhibitor, buffer solutions, stabilizing agent, diluting agent, or rinsing reagent.

\* \* \* \* \*